United States Patent [19]

Gross

[11] Patent Number: Plant 7,733

[45] Date of Patent: Dec. 3, 1991

[54] POINSETTIA NAMED GROJIBI

[76] Inventor: Eduard Gross, 16250 Blanzac, Nanteuillet, France

[21] Appl. No.: 446,881

[22] Filed: Dec. 6, 1989

[51] Int. Cl.[5] ..... A01H 5/00

[52] U.S. Cl. ..... Plt./86

[58] Field of Search ..... Plt./86

[56] References Cited

U.S. PATENT DOCUMENTS

P.P. 6,592 2/1989 Gross ..... Plt. 86

*Primary Examiner*—James R. Feyrer

*Attorney, Agent, or Firm*—Jordan and Hamburg

[57] ABSTRACT

A new Poinsettia cultivar distinguished by large, bright pink bracts, large, thick stems and leaves and a short growth habit is herein described. The stems of this plant are noticeably strong with short internodes, yet possessing a strong self-branching habit. As a flowering potted plant, it performs equally well as a single-stemmed, unpinched plant or a branched, pinched plant.

1 Drawing Sheet

BACKGROUND OF THE NEW PLANT

This new Poinsettia originated as a sport and was produced by me in my greenhouses in Nanteuillet, Blanzac, France. I selected this plant because of its large bright pink bracts, thick green leaves and thick pink bracts, short growth habit, thick, strong stems and self-branching characteristics. This new Poinsettia flowers equally well as either a pinched, multiple branched plant or as an unpinched single stem plant. The plant's characteristics are unique, resulting in a plant which is recognizable as being different from any other poinsettia cultivar. I propagated this new plant by vegetative cuttings through successive generations, which time and again has shown its thick stems and leaves, short stature and bright pink bracts which have remained unchanged from generation to generation.

DESCRIPTION OF THE DRAWING

My new variety of Poinsettia is illustrated by the accompanying full color photographic drawing, the color being as true to that herein specified as is reasonably possible to obtain by conventional photographic procedures.

DESCRIPTION OF THE NEW PLANT

The following is a detailed description of this new poinsettia as observed under greenhouse culture in Nanteuillet, Blanzac, France. Color designations are according to The R.H.S. Colour Chart published in 1966 by The Royal Horticultural Society at London, England.

THE PLANT

Origin: Spontaneous sport of "Supjibi," the latter being the subject of U.S. Plant Pat. No. 6,592, issued Feb. 7, 1989.

Classification:

*Botanic.—Euphorbia pulcherrima.*

Form: Shrub.

Height: Typically 135 cm after one year.

Growth habit: As a single stem, upright, but short. Leaves and bracts are unusually thick and large. The stems are thick and strong with closely spaced nodes. I observed flowering stems of 30–36 cm length with pink bract presentations 25–30 cm in diameter.

Branching: Upright with many stems producing a compact, bushy plant full in appearance.

Growth rate: Very fast. No growth regulator is needed. Rooting of vegetative cuttings occurs in 15–20 days under intermittent mist and the plant will flower in about 8 weeks under continuous long night conditions and night temperatures of 16°–18° C. The number of branches presented after pinching is normally 6–8.

Foliage: This plant has unusually large, thick and erect leaves having a dark green upper side and a light green underside, with the plane of the leaf blade nearly perpendicular to the stem. There is no leaf torsion. The leaves have no hair. The larger leaves typically have leaf blades 12–16 cm long and 8–10 cm wide and leaf petioles 3–4 cm long. The length from the leaf base to the petiole base is typically 4 cm. The color of the petiole surface is light green.

Leaf shape: Typical mature leaves are lanceolate in overall shape with entire to weakly lobed margins, the apex of a mature leaf being acuminate in shape and the base thereof being ovate in shape.

Bracts: Generally there are 8 uniformly colored bright pink bracts, typically thicker and larger than most poinsettia cultivars. It is not unusual for the larger bract-leaf blades to be 12–15 and even up to 17 cm long and 10–12 cm wide with short leaf petioles, 3–4 cm long, which are light green in color. The short bract petioles result in a bract presentation with a close, tight center. The large lower bracts are somewhat cascading while the plane of the smaller bract blades is nearly perpendicular to the stem axis.

Shape: In overall shape, the bracts are usually ovate with entire margins and have an acute apex and a rotundate base.

Color:

*Upper side.*—RHS 51B near the border and 52A/B in the middle.

*Under side.*—RHS 51C/D.

The cyathia are very large, light orange in color and have one or two nectar cups.

I claim:

1. A new and distinctive Poinsettia cultivar, substantially as herein shown and described, particularly distinguished by large, bright pink bracts, large thick stems and leaves and a short, self-branching growth habit.

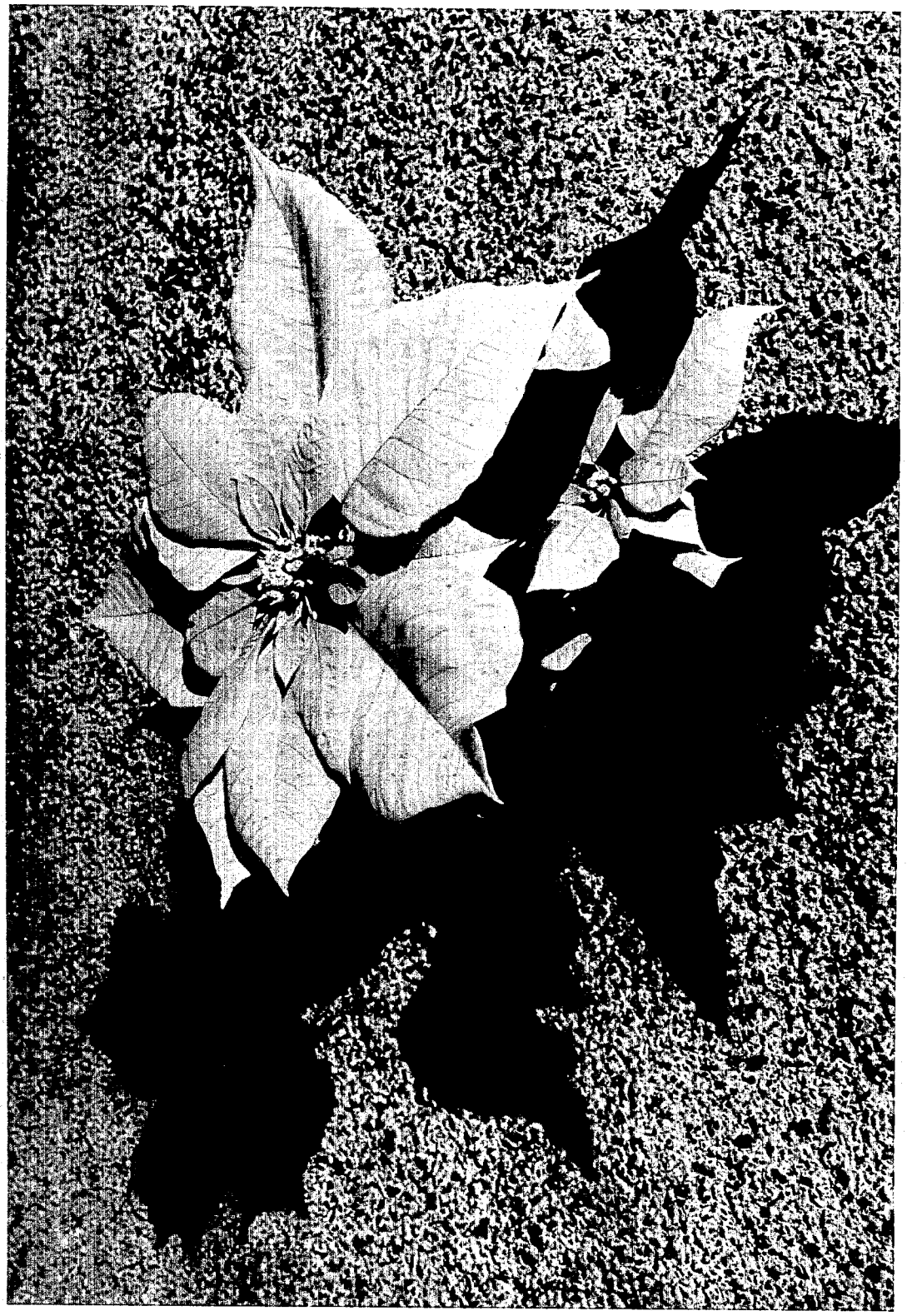

* * * * *